United States Patent
Bohen et al.

(10) Patent No.: US 9,427,390 B2
(45) Date of Patent: *Aug. 30, 2016

(54) METHOD FOR FORMING VOLUMIZING, FIXATIVE, AND CONDITIONING PARTICLES FOR FINE HAIR

(71) Applicant: ELC Management LLC, Melville, NY (US)

(72) Inventors: John Michael Bohen, Lino Lakes, MN (US); Amy Christine Anderson-Gaber, Saint Paul, MN (US); Anita Marie Grahn, Blaine, MN (US)

(73) Assignee: ELC Management LLC, Melville, NY (US)

(*) Notice: Subject to any disclaimer, the term of this patent is extended or adjusted under 35 U.S.C. 154(b) by 449 days.

This patent is subject to a terminal disclaimer.

(21) Appl. No.: 13/759,417

(22) Filed: Feb. 5, 2013

(65) Prior Publication Data

US 2014/0219944 A1    Aug. 7, 2014

Related U.S. Application Data

(60) Provisional application No. 61/596,506, filed on Feb. 8, 2012.

(51) Int. Cl.
*A61K 8/73* (2006.01)
*A61K 8/55* (2006.01)
*A61Q 5/12* (2006.01)
*A61Q 5/02* (2006.01)
*A61Q 5/06* (2006.01)
*A61K 8/02* (2006.01)

(52) U.S. Cl.
CPC .............. *A61K 8/732* (2013.01); *A61K 8/0241* (2013.01); *A61K 8/553* (2013.01); *A61K 8/73* (2013.01); *A61Q 5/02* (2013.01); *A61Q 5/06* (2013.01); *A61Q 5/12* (2013.01)

(58) Field of Classification Search
CPC .................................................... A61K 8/0295
USPC ......................................................... 424/70.13
See application file for complete search history.

(56) References Cited

U.S. PATENT DOCUMENTS

| 5,858,938 A | 1/1999 | Glenn et al. |
|---|---|---|
| 2002/0034486 A1 | 3/2002 | Midha et al. |
| 2005/0227911 A1 | 10/2005 | Goldshtein et al. |
| 2006/0002880 A1 | 1/2006 | Peffly et al. |
| 2006/0251602 A1 | 11/2006 | Goddinger et al. |
| 2009/0060849 A1 | 3/2009 | Song et al. |
| 2011/0182956 A1 | 7/2011 | Glenn, Jr. et al. |
| 2011/0212145 A1 | 9/2011 | Wheeler et al. |
| 2012/0021025 A1 | 1/2012 | Bendejacq et al. |

FOREIGN PATENT DOCUMENTS

| WO | WO-2006/017827 | 2/2006 |
|---|---|---|
| WO | PCT-2012-012084 A2 | 1/2012 |

OTHER PUBLICATIONS

Anonymous: "CELQUAT LS-50 Polymer—AkzoNobel Personal Care"; Aug. 13, 2015; XPO55207575; Retreived from the Internet: URL: http://www.sc.akzonobel.com/en/personalcare/Pages/product-detail.aspx?prodID=6633; Retreived on Aug. 13, 2015.
Supplementary European Search Report: EP13746538.1; Completion Date: Aug. 13, 2015; Mailing Date: Aug. 21, 2015.

*Primary Examiner* — Jake Vu
(74) *Attorney, Agent, or Firm* — Idris McKelvey

(57) ABSTRACT

A method for forming a large particle complex comprising the steps of combining a hydrolyzed corn starch polymer, a starch/cellulose polymer, a hydrogenated phospholipid, and gum arabic in a cosmetically acceptable carrier to form a premix composition; heating said premix to about 85° C. for about 15 minutes; and cooling the composition to room temperature. The particle complex is useful as a component of a sprayable composition which provides volumizing, hair fixing, and conditioning as a leave-on treatment for human hair.

11 Claims, No Drawings

METHOD FOR FORMING VOLUMIZING, FIXATIVE, AND CONDITIONING PARTICLES FOR FINE HAIR

CROSS-REFERENCE TO RELATED APPLICATIONS

The present application claims priority from U.S. Provisional Application No. 61/596,506, filed Feb. 8, 2012.

FIELD OF THE INVENTION

The present invention relates to personal care compositions comprising a conditioning particle complex. More particularly, the present invention relates a method for forming a large particle complex comprising hydrolyzed corn starch, starch/cellulose polymer, hydrogenated phospholipid, and gum arabic. The particle complex is capable of delivering volumizing, fixative, and conditioning benefits as a component of a sprayable leave-on personal care composition.

BACKGROUND OF THE INVENTION

People with fine or thin hair often use "volumizing" shampoos in order to add volume and body to their hair. Conventional volumizing shampoos, however, possess certain drawbacks such as, for example, a failure to provide real volume benefits as the effective ingredients are too heavy on the hair, thereby weighing it down. Another drawback associated with volumizing shampoos is their inability to provide appreciable styling attributes and wet-conditioning onto hair treated therewith.

Most products achieve their volumizing benefits by combining various synthetic ingredients based on combinations of polyvinyl pyrrolidone (PVP), vinyl acetate (VA), and acrylates to form a film on the hair to add volume, hold and style. But consumers increasingly desire volumizing compositions which provide volume with natural ingredients.

Thus, there is an ongoing need for naturally-based hair care compositions which confer volume to the hair, improve the styling attributes and enhance the wet combability, and which do not leave the hair stiff or excessively sticky.

SUMMARY OF THE INVENTION

A method for forming a large particle complex comprising the steps of combining a hydrolyzed corn starch polymer, a starch/cellulose polymer, a hydrogenated phospholipid, and gum arabic in a cosmetically acceptable carrier to form a premix composition; heating said premix to about 85° C. for about 15 minutes; and cooling the composition to room temperature.

The particle complex is useful as a component of a sprayable composition which provides volumizing, hair fixing, and conditioning as a leave-on treatment for human hair.

DETAILED DESCRIPTION OF THE INVENTION

While the specification concludes with claims that particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level, and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "polymer" as used herein shall include materials whether made by polymerization of one type of monomer or made by two (i.e., copolymers) or more types of monomers.

The term "solid particle" as used herein means a particle that is not a liquid or a gas.

The term "water-soluble" as used herein, means that the polymer is soluble in water in the present composition. In general, the polymer should be soluble at 25° C. at a concentration of at least 0.1% by weight of the water solvent, preferably at least 1%, more preferably at least 5%, most preferably at least 15%.

The term "water-insoluble" as used herein, means that a compound is not soluble in water in the present composition. Thus, the compound is not miscible with water.

Hydrolyzed Starch Polymer

The personal care compositions of the present invention comprise water-soluble hydrolyzed starch polymers. As used herein, the term "hydrolyzed" refers to a starch which is degraded, for example, by enzymes (incomplete hydrolysis) or acid (complete hydrolysis).

The personal care compositions comprise hydrolyzed starch polymers at a range of about 0.01% to about 10%, and more preferably from about 1% to about 7%, and most preferably from about 2% to about 4% by weight of the composition.

The hydrolyzed starch polymers generally have a molecular weight from about 250,000 to about 15,000,000. As used herein, the term "molecular weight" refers to the weight average molecular weight. The weight average molecular weight may be measured by gel permeation chromatography ("GPC") using a Waters 600E HPLC pump and Waters 717 auto-sampler equipped with a Polymer Laboratories PL Gel MIXED-A GPC column (Part Number 1110-6200, 600×7.5 mm, 20 um) at a column temperature of 55° C. and at a flow rate of 1.0 ml/min (mobile phase consisting of Dimethylsulfoxide with 0.1% Lithium Bromide), and using a Wyatt DAWN EOS MALLS (multi-angle laser light scattering detector) and Wyatt Optilab DSP (interferometric refractometer) detectors arranged in series (using a dn/dc of 0.066), all at detector temperatures of 50° C., with a method created by using a Polymer Laboratories narrow dispersed Polysaccharide standard (Mw=47,300), with an injection volume of 200 μl.

The hydrolyzed starch polymers may comprise maltodextrin. Thus, in one embodiment of the present invention, the hydrolyzed starch polymers may be further characterized by a Dextrose Equivalance ("DE") value of less than about 35, and more preferably from about 1 to about 20. The DE value is a measure of the reducing equivalence of the hydrolyzed starch referenced to dextrose and expressed as a percent (on dry basis). Starch completely hydrolyzed to dextrose has a DE value of 100, and unhydrolyzed starch has a DE value of 0. A suitable assay for DE value includes one described in "Dextrose Equivalent", *Standard Analytical Methods of the Member Companies of the Corn Industries Research Foundation,* 1st ed., Method E-26. Additionally, the hydrolyzed starch polymers of the present invention may comprise a dextrin. Dextrin is typically a pyrolysis product of starch with a wide range of molecular weights.

The source of starch before hydrolysis can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, or mixtures thereof. Corn starch is preferred.

Suitable hydrolyzed starch for use in compositions of the present invention is available from known starch suppliers. Such starch polymers are described in U.S. Patent Publication No. 2011/0212145A1 to Wheeler et al. A particularly preferred starch polymer is Asensa® NFF11 from Honeywell.

Starch/Cellulose Polymer

The personal care compositions include at least one polymer which is a co-processed combination of starch and cationic cellulose. Suitable starch/cellulose combination polymers include, for example, Celquat® LS-50 from AkzoNobel. Celquat® LS-50 is more specifically a polyquaternium-4/hydroxypropyl starch copolymer blend.

The personal care compositions of the present invention comprise the starch/cellulose combination polymers at a range of about 0.01% to about 10%, more preferably from about 0.75% to about 8%, more preferably from about 1% to about 5%, and most preferably from about 1% to about 2.5% by weight of the composition.

Hydrogenated Phospholipid

The personal care compositions include at least hydrogenated phospholipid. Suitable hydrogenated phospholipids include those which are formed synthetically or, more preferably, by hydrogenation of naturally occurring phospholipids, e.g. phospholipids previously isolated from eggs or soy. Preferred hydrogenated phospholipids include hydrogenated lecithin such as Lecinol S-10, available from Barnet.

The personal care compositions of the present invention comprise the hydrogenated phospholipid at a level of from about 0.1% to about 2%, more preferably from about 0.2% to about 1.5%, and most preferably from about 0.3% to about 1.0% by weight of the composition.

Gum Arabic

The personal care compositions include gum arabic, which is also known as acacia gum. It is a natural gum derived from the hardened sap from the acacia tree. Gum arabic is generally sourced from two species of the acacia tree; Acacia Senegal and Acacia Seyal. Particularly preferred is gum arabic sourced from Acacia Senegal. Such gum arabic is commercially available under the tradename, TICorganic® Gum Arabic from TIC Gums.

The personal care compositions of the present invention comprise gum arabic at a level of from about 0.01% to about 3%, more preferably from about 0.02% to about 1.0%, and most preferably from about 0.08% to about 0.5% by weight of the composition.

Aqueous Carrier

The compositions also comprise an aqueous carrier. Preferably, the aqueous carrier is present in an amount of from about 50% to about 99.8% by weight of the personal care composition. The aqueous carrier comprises a water phase which can optionally include other liquid, water-miscible or water-soluble solvents such as co-surfactants and/or wetting agents.

Hair Conditioning Complex and Method

Method of Making

The compositions of the present invention include the aforementioned hydrolyzed corn starch, starch/cellulose polymer, hydrogenated phospholipid, and gum arabic which form a complex according to the compositions herein.

The complex may be formed by combining the hydrolyzed corn starch, starch/cellulose polymer, hydrogenated phospholipid, and gum arabic in an aqueous carrier to form a premix, prior to addition of other ingredients. The mixture is heated to about 85 degrees for about 15 minutes, during which time, additional water or oil soluble actives may optionally be added. Then the mixture is cooled to room temperature. Additional ingredients, including electrolytes, polymers, fragrance, and particles, may be added to the product at room temperature. The mixture is mixed under low shear throughout the entire process, but it is not homogenized.

In one embodiment, the compositions may be substantially free of volatile alcohols such as ethyl alcohol or isopropyl alcohol. The term, "substantially free" as used herein means that no more than trace amounts of a material may be present in the composition, and preferably none of a material is present in the composition.

Particle Complex

It is believed that mixing in the absence of homogenization forms a complex of relatively large particle size. The complex is comprised of the hydrogenated phospholipid, hydrolyzed starch polymer, gum arabic, and starch/cellulose polymer.

The complex, in solution, has an average particle size of from about 100 to 200 micrometers, more preferably from about 110 micrometers to about 190 micrometers, and most preferably from about 120 micrometers to about 180 micrometers.

It has been found that the complex forms most effectively when combined at particular ratios of one ingredient to another. For example, the hydrolyzed starch polymer is generally incorporated at a ratio of about 3:1 relative to the starch/cellulose polymer to form a first blend. The hydrogenated phospholipid is generally incorporated at a ratio of about 8:1 relative to the gum arabic to form a second blend. And the ratio of the first blend to the second blend is generally about 5:1 in the composition.

Importantly, the composition is not homogenized. Homogenization typically results in particles having a particle size of less than about 100 micrometers. It has been surprisingly discovered that formation of the complex herein, having a larger particle size, versus homogenized systems, provides enhanced sensory benefits to hair. Further, smaller particle sizes are generally thought to enhance sprayability of liquid compositions. But it has been found that the complex herein is highly sprayable even at its relatively high particle size. Particle size is measured using a Hydro S sample dispersion unit from Malvern.

The composition including the complex herein generally has a viscosity of from about 800 to about 1500 cps, preferably from about 900 to about 1400 cps. Viscosity is measured using a Brookfield LV viscometer according to the following specifications: LVT, spindle 2, 12 rpm, at 25° C.

Oily Conditioning Agent

In a preferred embodiment of the present invention, the personal care compositions comprise one or more oily conditioning agents. Oily conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the compositions of the present invention typically comprise a water-insoluble, water-dispersible, non-volatile, liquid that forms emulsified, liquid particles. Suitable oily conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

One or more oily conditioning agents are typically present at a concentration from about 0.01% to about 10%, preferably from about 0.1% to about 8%, more preferably from about 0.2% to about 4%, by weight of the composition.

Silicone Conditioning Agent

The oily conditioning agents of the compositions of the present invention are preferably a water-insoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 5,000 to about 1,500,000 csk, more preferably from about 10,000 to about 1,000,000 csk.

Non-volatile silicone oils suitable for use in compositions of the present invention may be selected from organo-modified silicones and fluoro-modified silicones. In one embodiment of the present invention, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

In a preferred embodiment of the present invention, the non-volatile silicone oil is dimethicone.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984). A particularly preferred silicone fluid is Dow Corning 1503 fluid.

Organic Conditioning Oils

The oily conditioning agent of the compositions of the present invention may also comprise at least one organic conditioning oil, either alone or in combination with other conditioning agents, such as the silicones described above.

Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include 2,2,4,4,6,6,8,8-dimethyl-10-methylundecane and 2,2,4,4,6,6-dimethyl-8-methylnonane, available from Permethyl Corporation. A preferred hydrocarbon polymer is polybutene, such as the copolymer of isobutylene and butene, which is commercially available as L-14 polybutene from Amoco Chemical Corporation.

Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

Fatty Esters

Other suitable organic conditioning oils for use as the conditioning agent in the compositions of the present invention include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are those known as polyhydric alcohol esters. Such polyhydric alcohol esters include alkylene glycol esters.

Still other fatty esters suitable for use in the compositions of the present invention are glycerides, including, but not limited to, mono-, di-, and tri-glycerides, preferably di- and tri-glycerides, more preferably triglycerides. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones. Specific non-limiting examples of suitable fluorinated compounds include the Fomblin product line from Ausimont which includes HC/04, HC/25, HC01, HC/02, HC/03; Dioctyldodecyl Fluoroeptyl Citrate, commonly called Biosil Basics Fluoro Gerbet 3.5 supplied by Biosil Technologies; and Biosil Basics Fluorosil LF also supplied by Biosil Technologies.

Alkyl Glucosides and Alkyl Glucoside Derivatives

Suitable organic conditioning oils for use in the personal care compositions of the present invention include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

Additional Components

The personal care compositions of the present invention may further comprise one or more additional components known for use in hair care or personal care products, provided that the additional components are physically and chemically compatible with the essential components described herein, or do not otherwise unduly impair product stability, aesthetics or performance. Individual concentrations of such additional components may range from about 0.001% to about 10% by weight of the personal care compositions.

Non-limiting examples of additional components for use in the composition include natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

Cellulose or Guar Cationic Deposition Polymers

The personal care compositions of the present invention may also include cellulose or guar cationic deposition polymers. Cellulose or galactomannan cationic deposition polymers are preferred. Generally, such cellulose or guar cationic deposition polymers may be present at a concentration from about 0.05% to about 5%, by weight of the composition. Suitable cellulose or guar cationic deposition polymers have a molecular weight of greater than about 5,000. Preferably, the cellulose or guar cationic deposition polymers have a molecular weight of greater than about 200,000. Additionally, such cellulose or guar deposition polymers have a charge density from about 0.15 meq/g to about 4.0 meq/g at the pH of intended use of the personal care composition, which pH will generally range from about pH 3 to about pH 9, preferably between about pH 4 and about pH 8. The pH of the compositions of the present invention are measured neat.

Suitable cellulose or guar cationic polymers include those which conform to the following formula:

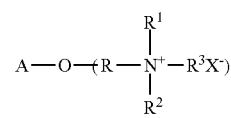

wherein A is an anhydroglucose residual group, such as a cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, the cellulose or guar cationic polymers are salts of hydroxyethyl cellulose reacted with trimethyl ammonium substituted epoxide, referred to in the industry (CTFA) as Polyquaternium 10 and available from Amerchol Corp. (Edison, N.J., USA).

Particles

The compositions of the present invention optionally may comprise additional particles. Preferably, particles useful in the present invention are dispersed water-insoluble particles. Particles useful in the present invention can be inorganic, synthetic, or semi-synthetic. In the compositions of the present invention, it is preferable to incorporate no more than about 20%, more preferably no more than about 10% and even more preferably no more than 2%, by weight of the composition, of particles. In an embodiment of the present invention, the additional particles have an average particle size of less than about 300 μm.

Non-limiting examples of inorganic particles include colloidal silicas, fumed silicas, precipitated silicas, silica gels, magnesium silicate, glass particles, talcs, micas, sericites, and various natural and synthetic clays including bentonites, hectorites, and montmorillonites.

Examples of synthetic particles include silicone resins, poly(meth)acrylates, polyethylene, polyester, polypropylene, polystyrene, polyurethane, polyamide (e.g., Nylon®), epoxy resins, urea resins, acrylic powders, and the like.

Non-limiting examples of hybrid particles include sericite & crosslinked polystyrene hybrid powder, and mica and silica hybrid powder.

Opacifying Agents

The compositions of the present invention may also contain one or more opacifying agents. Opacifying agents are typically used to impart desired aesthetic benefits to the composition, such as color or pearlescence. In the compositions of the present invention, it is preferable to incorporate no more than about 20%, more preferably no more than about 10% and even more preferably no more than 2%, by weight of the composition, of opacifying agents.

Suitable opacifying agents include, for example, fumed silica, polymethylmethacrylate, micronized Teflon®, boron nitride, barium sulfate, acrylate polymers, aluminum silicate, aluminum starch octenylsuccinate, calcium silicate, cellulose, chalk, corn starch, diatomaceous earth, Fuller's earth, glyceryl starch, hydrated silica, magnesium carbonate, magnesium hydroxide, magnesium oxide, magnesium trisilicate, maltodextrin, microcrystalline cellulose, rice starch, silica, titanium dioxide, zinc laurate, zinc myristate, zinc neodecanoate, zinc rosinate, zinc stearate, polyethylene, alumina, attapulgite, calcium carbonate, calcium silicate, dextran, nylon, silica silylate, silk powder, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The opacifying agents may also comprise various organic and inorganic pigments. The organic pigments are generally various aromatic types including azo, indigoid, triphenylmethane, anthraquinone, and xanthine dyes. Inorganic pigments include iron oxides, ultramarine and chromium or chromium hydroxide colors, and mixtures thereof.

Suspending Agents

The compositions of the present invention may further comprise a suspending agent at concentrations effective for suspending water-insoluble material in dispersed form in the compositions or for modifying the viscosity of the composition. Such concentrations generally range from about 0.1% to about 10%, preferably from about 0.3% to about 5.0%, by weight of the composition, of suspending agent.

Suspending agents useful herein include anionic polymers and nonionic polymers. Useful herein are vinyl polymers such as cross linked acrylic acid polymers with the CTFA name Carbomer.

Paraffinic Hydrocarbons

The compositions of the present invention may contain one or more paraffinic hydrocarbons. Paraffinic hydrocarbons suitable for use in compositions of the present invention include those materials which are known for use in hair care or other personal care compositions, such as those having a vapor pressure at 1 atm of equal to or greater than about 21° C. (about 70° F.). Non-limiting examples include pentane and isopentane.

Propellants

The composition of the present invention also may contain one or more propellants. Propellants suitable for use in compositions of the present invention include those materials which are known for use in hair care or other personal care compositions, such as liquefied gas propellants and compressed gas propellants. Suitable propellants have a vapor pressure at 1 atm of less than about 21° C. (about 70° F.). Non-limiting examples of suitable propellants are alkanes, isoalkanes, haloalkanes, dimethyl ether, nitrogen, nitrous oxide, carbon dioxide, and mixtures thereof.

Other Optional Components

The compositions of the present invention may contain fragrance.

The compositions of the present invention may also contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts.

The compositions of the present invention may contain a mono- or divalent salt such as sodium chloride.

The compositions of the present invention may also contain chelating agents.

The compositions of present invention may further comprise materials useful for hair loss prevention and hair growth stimulants or agents.

EXAMPLES

All parts, percentages, and ratios herein are by weight unless otherwise specified. Some components may come from suppliers as dilute solutions. The levels given reflect the weight percent of the active material, unless otherwise specified.

Method of Treating Hair or Skin

The personal care compositions of the present invention are used in a conventional manner for conditioning, styling, and volumizing hair. Generally, a method of treating hair of the present invention comprises applying the composition to the hair. More specifically, an effective amount of the personal care composition is applied to the hair, which has preferably been wetted with water, and preferably shampooed. The composition is applied to hair via an aerosol or pump-type sprayer in an amount effective to achieve conditioning, volumizing, and hair fixing benefits. Such effective amounts generally range from about 1 g to about 50 g, preferably from about 1 g to about 20 g. Application to the hair typically includes working the composition through the hair such that most or all of the hair is contacted with the composition. It is not necessary to rinse the composition from hair after application as it is preferably used as a leave-in composition.

Non-Limiting Examples

The compositions illustrated in the following Examples illustrate specific embodiments of the compositions of the present invention, but are not intended to be limiting thereof. Other modifications can be undertaken by the skilled artisan without departing from the spirit and scope of this invention. These exemplified embodiments of the composition of the present invention provide enhanced deposition of conditioning agents to the hair and/or skin.

The compositions illustrated in the following Examples are prepared by conventional formulation and mixing methods, an example of which is described above. All exemplified amounts are listed as weight percents and exclude minor materials such as diluents, preservatives, color solutions, imagery ingredients, botanicals, and so forth, unless otherwise specified.

The following are representative of shampoo compositions of the present invention:

| EXAMPLE COMPOSITION | 1 | 2 | 3 | 4 | 5 | 6 | 7 |
|---|---|---|---|---|---|---|---|
| Hydrolyzed Starch[1] | 3.00 | 2.00 | 2.00 | 8.00 | 5.00 | 1.50 | 3.00 |
| Zema Propanediol[2] | 2.00 | 1.00 | 1.00 | — | 1.00 | 1.00 | 1.00 |
| Dimethicone PEG-8 Meadowfoamate[3] | 1.50 | — | 1.50 | 0.50 | 0.50 | 0.50 | 0.50 |
| Polyquaternium-4/Hydroxypropyl Starch Copolymer[4] | 1.25 | 1.50 | 1.50 | 6.00 | 1.50 | 3.00 | 1.50 |
| Montanov™ 82[5] | 1.00 | 1.00 | 1.00 | — | 1.00 | 1.00 | 1.00 |
| Dimethiconol/Dimethicone Fluid[6] | 1.00 | 1.00 | — | 1.00 | 1.00 | — | — |
| Hydrogenated Lecithin[7] | 0.80 | 1.00 | 1.50 | 0.50 | 1.00 | 0.70 | 1.00 |
| Gum Arabic[8] | 0.10 | 2.00 | 1.00 | 0.50 | 0.8 | 0.3 | .01 |
| Fragrance | 0.7 | 0.7 | 0.7 | 0.7 | 0.7 | 0.7 | 0.7 |
| Preservatives, pH adjusters | Up to 2 | Up to 2 | Up to 2 | Up to 2 | Up to 2 | Up to 2 | Up to 2 |
| Water | q.s. | q.s. | q.s. | q.s. | q.s. | q.s. | q.s. |

[1]Asensa NFF 11, supplier: Honeywell
[2]Supplier: DuPont Tate & Lyle BioProducts
[3]Fancorsil Lim-1, supplier: Elementis Specialties
[4]Celquat ® LS-50 supplier: AkzoNobel
[5]supplier: Seppic
[6]Dow Corning ® 1503 Fluid, supplier Dow Corning
[7]Lecinol S-10, supplier: Barnet The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a large particle complex comprising the steps of:
    a) combining a hydrolyzed corn starch polymer, a starch/cellulose polymer, a hydrogenated phospholipid, and gum arabic in a cosmetically acceptable carrier to form a premix composition;
    b) heating said premix to about 85° C. for about 15 minutes; and
    c) cooling said composition to room temperature.

2. A method according to claim 1, wherein said hydrogenated phospholipid is hydrogenated lecithin.

3. A method according to claim 1, wherein said hydrolyzed corn starch polymer and said starch/cellulose polymer are present at a ratio of about 3:1 to form a first blend.

4. A method according to claim 3, wherein said hydrogenated phospholipid and gum arabic are present at a ratio of about 8:1 to form a second blend.

5. A method according to claim 4, wherein said first blend and said second blend are present at a ratio of about 5:1.

6. A method according to claim 1, wherein the particle size of said particle complex is from about 100 micrometers to about 200 micrometers.

7. A method according to claim 1, further comprising at least one oily conditioning agent.

8. A method according to claim 7, wherein said oily conditioning agent is selected from the group consisting of silicones, organic conditioning oils, and mixtures thereof.

9. A method according to claim 1, wherein said composition is substantially free of volatile alcohols.

10. A method to claim 1, wherein said composition further comprises one or more additional ingredients selected from the group consisting of natural cationic deposition polymers, synthetic cationic deposition polymers, anti-dandruff agents, particles, suspending agents, paraffinic hydrocarbons, propellants, viscosity modifiers, dyes, non-volatile solvents, diluents, pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

11. A method according to claim 1, wherein said composition is not homogenized.

* * * * *